US010251720B1

(12) United States Patent
Hacker

(10) Patent No.: US 10,251,720 B1
(45) Date of Patent: Apr. 9, 2019

(54) SURGICAL SCALPEL HANDLE ASSEMBLY SYSTEM AND METHOD FOR REQUIRING A VERIFICATION PROCESS

(71) Applicant: Steven M. Hacker, Delray Beach, FL (US)

(72) Inventor: Steven M. Hacker, Delray Beach, FL (US)

(73) Assignee: Nano 2.0 Business Press, LLC, Delray Beach, FL (US)

( * ) Notice: Subject to any disclaimer, the term of this patent is extended or adjusted under 35 U.S.C. 154(b) by 232 days.

(21) Appl. No.: 15/489,024

(22) Filed: Apr. 17, 2017

Related U.S. Application Data

(63) Continuation-in-part of application No. 14/078,559, filed on Nov. 13, 2013, now Pat. No. 9,622,772.

(51) Int. Cl.
| | |
|---|---|
| *A61B 1/06* | (2006.01) |
| *B26B 5/00* | (2006.01) |
| *A61B 50/20* | (2016.01) |
| *A61B 17/3211* | (2006.01) |

(52) U.S. Cl.
CPC ............... *A61B 50/20* (2016.02); *A61B 1/06* (2013.01); *A61B 17/3211* (2013.01); *B26B 5/001* (2013.01); *A61B 2017/32113* (2013.01); *Y10T 403/7007* (2015.01)

(58) Field of Classification Search
CPC .... A61B 2090/0807; A61B 2090/0811; A61B 2090/32113; A61B 17/3211; A61B 17/3213; A61B 2017/32116; A61B 2017/32113; A61B 1/06; B26B 5/001; B26B 5/002; B26B 5/003; B26B 1/08; A61F 9/013

USPC ............. 30/162; 606/167; 116/286; 40/334, 40/905; 401/192, 194; 362/23.01
See application file for complete search history.

(56) References Cited

U.S. PATENT DOCUMENTS

| | | | | |
|---|---|---|---|---|
| 2,607,987 | A | * | 8/1952 | Bettenhausen ......... B26B 5/003 30/162 |
| 2,735,176 | A | * | 2/1956 | Costin ...................... A61D 1/00 30/162 |
| 2,971,283 | A | * | 2/1961 | Parker .................. B43K 24/084 40/334 |
| 3,905,101 | A | * | 9/1975 | Shepherd ........... A61B 17/3213 30/162 |
| 3,906,626 | A | * | 9/1975 | Riuli .................. A61B 17/3213 30/162 |

(Continued)

*Primary Examiner* — Laura M Lee
(74) *Attorney, Agent, or Firm* — Nancy J. Flint, Attorney at Law, P.A.; Nancy J. Flint, Esq.

(57) ABSTRACT

A surgical scalpel handle assembly system and method that requires a surgeon to actively perform a verification process known as a "time out" verification process but specifically requires sequentially moving a series of actuator knobs on a scalpel handle upon affirming each criterion embedded in the scalpel handle. The required sequential confirmation of each criterion unlocks and ejects a blade holder from a scalpel handle to a position fully engaged and ready for blade attachment, surgery and in cutting position. The assembly system and method includes exposed visual indicia on the handle that indicates green exposed visual indices upon affirming verification of "time out" criteria and thus triggering the deployment of a fully exposed, engaged, and in a ready for surgery for blade attachment in handle.

7 Claims, 10 Drawing Sheets

SLIDER #3 MOVED TO
CONFIRMED POSITION AND
BAYONET EJECTED (SHOWN
WITH BLADE)

(56) References Cited

U.S. PATENT DOCUMENTS

| | | | | |
|---|---|---|---|---|
| 5,431,672 | A * | 7/1995 | Cote | A61B 17/3211 30/167 |
| 5,779,724 | A * | 7/1998 | Werner | A61B 17/3211 30/162 |
| 6,048,354 | A * | 4/2000 | Lawrence | A61B 17/3211 606/167 |
| 6,629,985 | B1 * | 10/2003 | Kiehne | A61B 17/3213 30/162 |
| 6,645,216 | B2 * | 11/2003 | Masury | A61B 17/3211 30/162 |
| 6,742,953 | B2 * | 6/2004 | Burden | B43K 29/007 401/192 |
| 6,757,977 | B2 * | 7/2004 | Dambal | A61B 17/3211 30/162 |
| 7,153,317 | B2 * | 12/2006 | Kanodia | A61B 17/3211 606/167 |
| 7,189,207 | B2 * | 3/2007 | Viola | A61B 10/0275 600/564 |
| 7,201,760 | B2 * | 4/2007 | Masury | A61B 17/3211 30/162 |
| 9,072,541 | B2 * | 7/2015 | Hacker | A61B 17/3211 |
| 2003/0153938 | A1 * | 8/2003 | Masury | A61B 17/3211 606/167 |
| 2005/0177183 | A1 * | 8/2005 | Thorne | A61B 17/32 606/167 |
| 2007/0088374 | A1 * | 4/2007 | Masury | A61B 17/3211 606/167 |
| 2010/0168773 | A1 * | 7/2010 | Funderburk | A61B 17/3213 606/167 |
| 2011/0083326 | A1 * | 4/2011 | Sullivan | B26B 1/08 30/162 |
| 2013/0150785 | A1 * | 6/2013 | Heacock | C09K 9/02 604/111 |

* cited by examiner

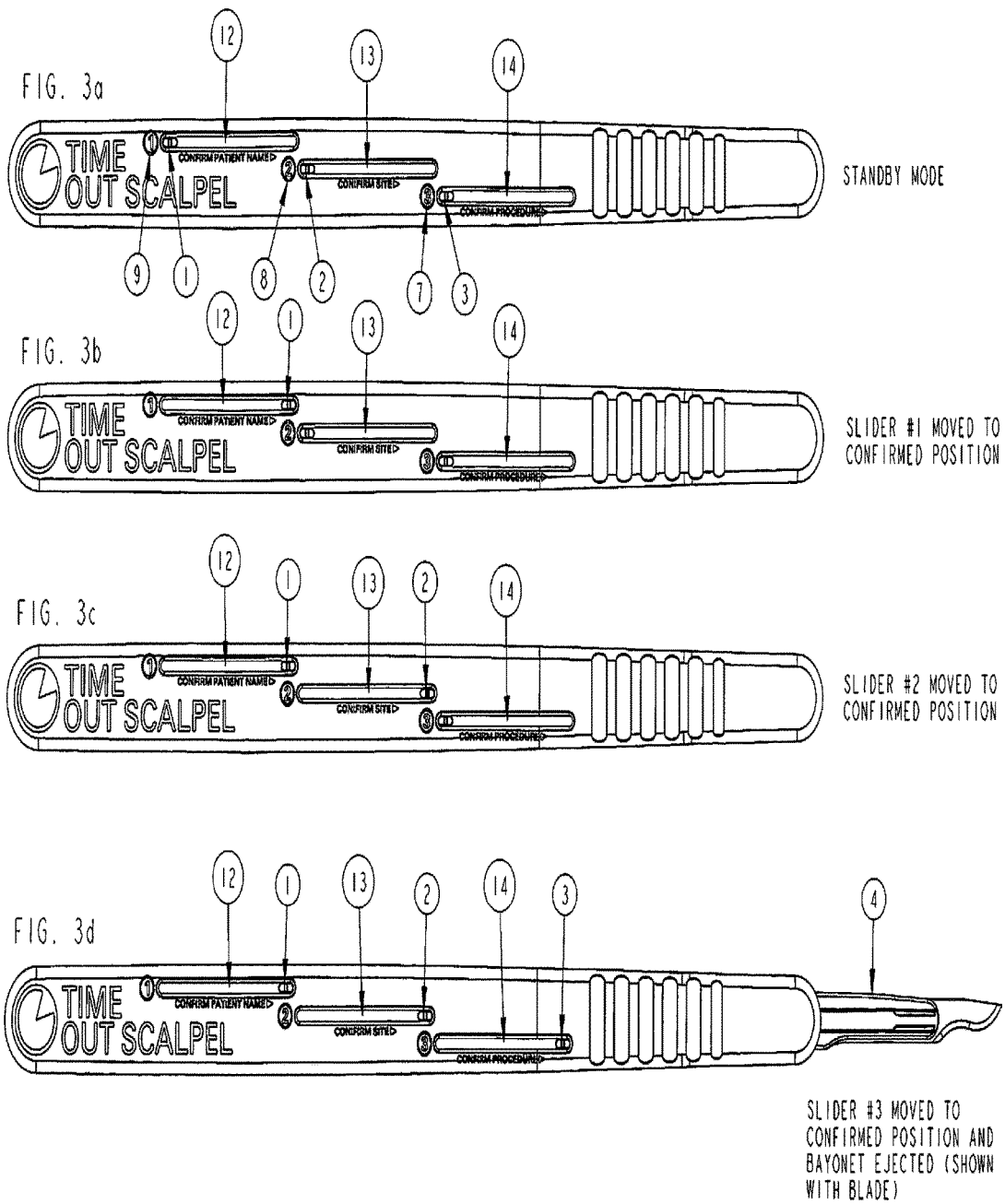

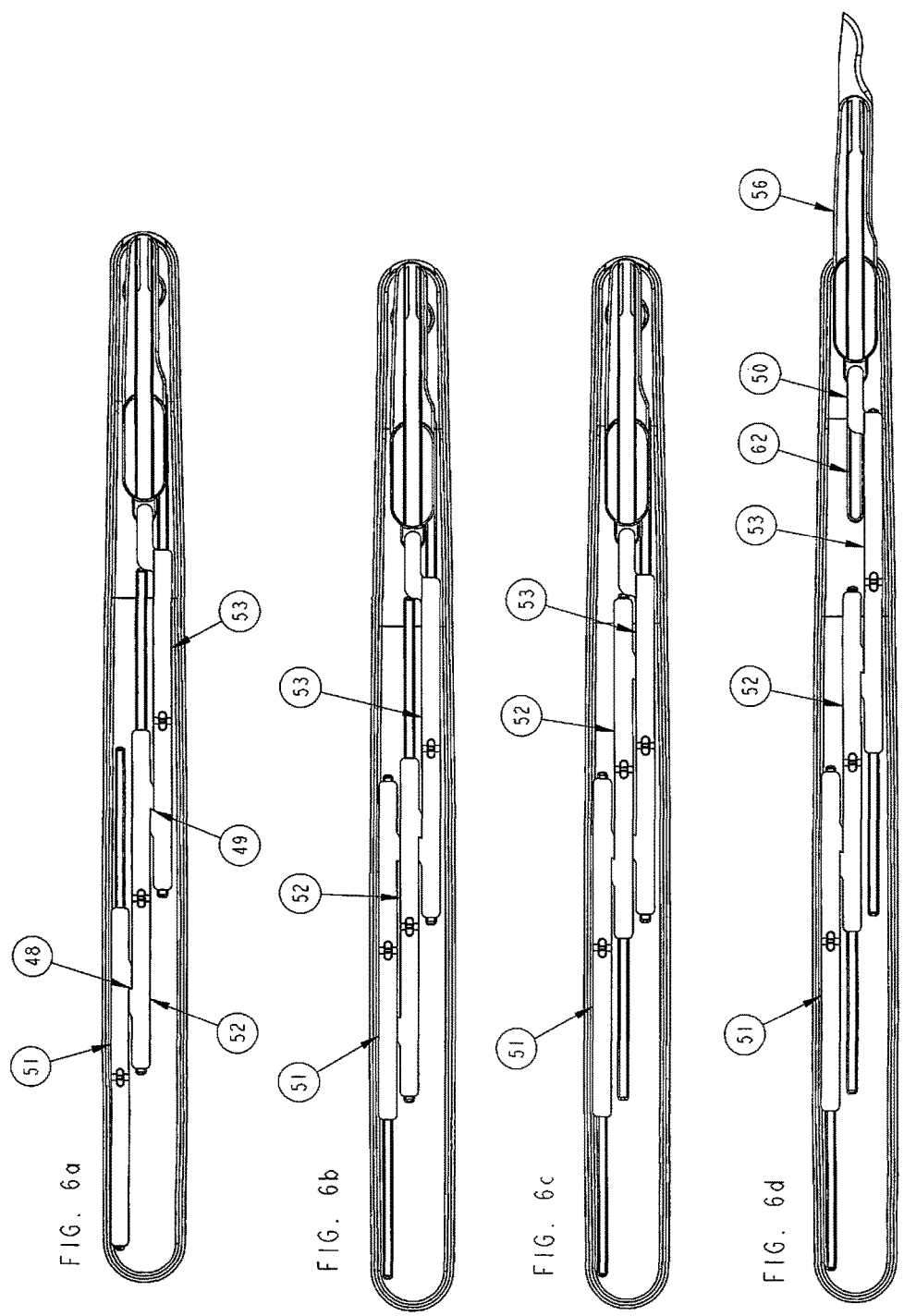

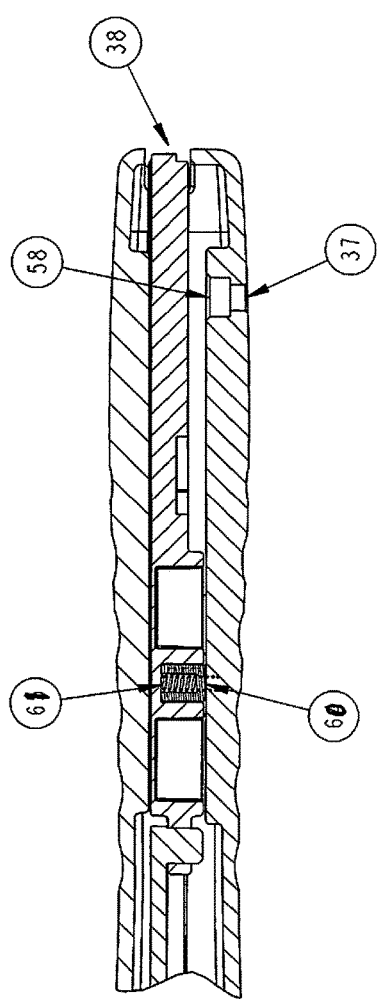
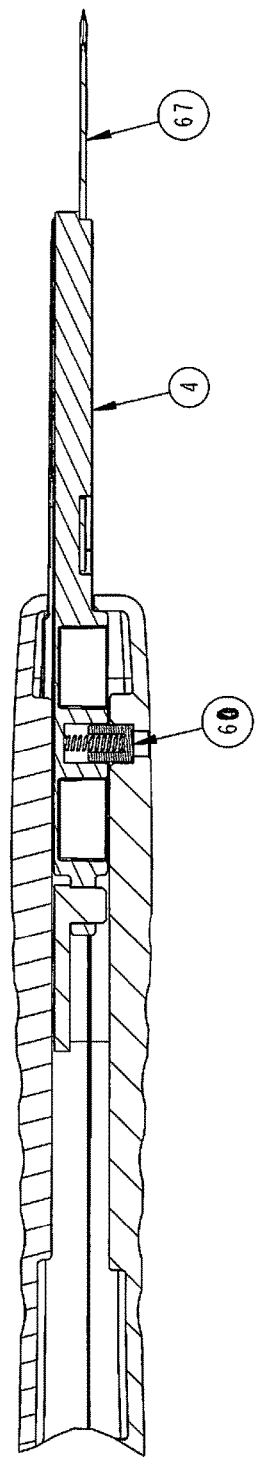
FIG. 8a
FIG. 8b

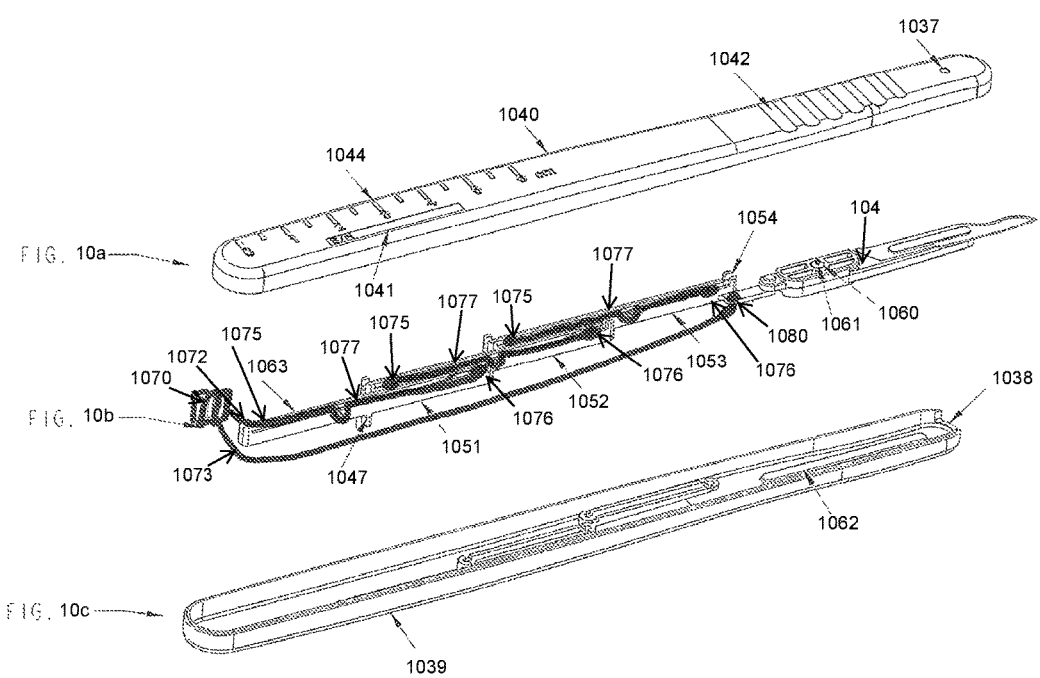

SURGICAL SCALPEL HANDLE ASSEMBLY SYSTEM AND METHOD FOR REQUIRING A VERIFICATION PROCESS

FIELD OF THE INVENTION

The present invention relates to the field of surgical incision, excision and biopsy instruments. In particular, this invention relates to a surgical scalpel handle that requires the surgeon to use various actuators on a scalpel handle, specifically, actively move actuator knobs in affirmation of a surgical "time out" verification process on the scalpel handle, interpret visual indices on the handle, and eventually eject a movable blade holder from within the handle into ready for blade attachment and ready for cutting position.

BACKGROUND OF THE INVENTION

The present invention is directed to a surgical scalpel handle and blade assembly system and method for requiring a surgical time out verification process be performed with actuator knobs on a scalpel handle prior to performing surgery when using a scalpel handle.

Physicians and surgeons use a scalpel handle to attach to a blade to excise human tissue for a variety of purposes.

Wrong site surgery can be disastrous psychologically for the patient, at the least, and result in death at its worst. Wrong site surgery by surgeons is common and a felt to be significantly underreported because of confidential data, embarrassment and legal liability. There is zero tolerance amongst patients and surgeons for wrong site, wrong person, and wrong procedure surgery errors. Yet, it is still projected to occur thousands of times each year. Wrong site surgery may have minimal health consequences in patients undergoing minor skin surgery but can be disastrous in those undergoing less minor surgery. Regardless of the level of surgery, for the patient, wrong site surgery is distressing and frightening. Wrong site surgery including wrong person surgery occurs not only in the operating room but also in a physician's office or surgery center. In fact, the Joint Commission on the Accreditation of Health Care Organizations instituted a Universal Protocol that requires a "time out" taken by the surgeon prior to performing surgery to confirm the location and the patient for the planned surgery prior to performing the surgery.

Taking a "time-out" before operative and other invasive procedures (Including at the patient bedside) is a requirement of the Joint Commission on Accreditation of Healthcare Organizations (JCAHO) 2003 and the National Patient Safety Goals and a component of the new JCAHO Universal Protocol to prevent wrong site, wrong procedure, wrong person Surgery. This Universal Protocol was approved Jul. 18, 2003, by the JCAHO, and was implemented Jul. 1, 2004, for all JCAHO accredited Organizations that perform surgical or other types of invasive procedures.

These recommendations are suggested for surgery taking place in any setting. Organizations and or their surgeons that fail to implement these recommendations risk a special Type 1 recommendation when surveyed by the JCAHO and more important risk the more serious possibly life threatening implications of wrong site or wrong patient surgery.

A "Time out" immediately before starting the procedure means prior to the start of any surgical or invasive procedure, the surgeon and staff conduct a final verification process, using active—not passive communication—to perform a "time out," and to confirm the following:

1. Correct patient,
2. Confirm planned procedure and
3. Confirmed planned operative site.

Despite these requirements and recommendations, wrong site surgeries still happen each year because the "time out" is overlooked and often not performed as the surgeon or the surgical team still forgets or does not take the time to perform the "time out" verification process. In a study published in the Annals of Surgery in 2010, a significant difference was seen in the "time-out" not performed group of physicians as a root cause for wrong site (72%) versus wrong patient (0%) procedures and constituted 98.8% of all issues leading to wrong site occurrences. The conclusion of this study showed that main root causes leading to wrong patient procedures were related to lack of performing a "Time out" 72% of the time. 1 Strict adherence to taking a "Time out" is required to promote a zero-tolerance for these preventable sentinel events as wrong site surgeries are one of the top causes for adverse sentinel events during surgery.

In the art, surgical scalpels with blades are well known. Also, several methods are provided in the art to ensure that the scalpel during all of pre-use use and post use conditions is safe and does not cause accidental harm to the operator.

U.S. Pat. No. 2,735,176 discloses a surgical knife that is provided with a hollow handle which functions as a sheath for the blade that is extendable through sliding and retractable between a first cutting position and a second shielded position.

U.S. Pat. Nos. 3,905,101 and 3,906,626 disclose sheaths wherein the handle carrying the blade is slideable from a first protective position to a second cutting position.

U.S. Pat. No. 6,757,977 discloses a disposable surgical safety scalpel with a retractable blade inside a hollow handle with a novel locking and unlocking arrangement that enables easy and safe use in various conditions.

U.S. Pat. Nos. 7,153,317 and 6,629,985 disclose a disposable guarded surgical with a handle and blade fixed to it and a slideable mounted guard and a surgical scalpel with retractable guard, respectively. These solutions are addressing the problem of accidental injury to the operator when handling a scalpel.

But none of these solutions addresses the problem of a surgeon using a scalpel before performing a surgical time-out verification process and none of these solutions addresses the issues of wrong site surgeries or wrong patient surgeries when a surgeon uses the scalpel. All of these systems have the same disadvantage in that they do not require the surgeon to perform action on the scalpel handle as part of the surgical time out process in order to release a surgical blade holder and ready the scalpel for surgery. Further none of these solutions use the scalpel as an interactive messaging tool with a novel knob sliding mechanism and changing visual indices through windows in scalpel handle to reflect and alert surgeon that scalpel has changed from "stop" to "go" status prior to performing surgery and confirm that he and his surgical team has performed the required surgical time out verification process. Picking up the scalpel by the surgeon is the very last step before cutting the patient's skin and as such is the most appropriate time to conduct the surgical time out. Using a surgical time out verification process method requiring a non passive action by the surgeon and the surgical team through the use of the scalpel handle can help remove the "impulsivity" associated with a surgeon's attitude, overwhelming schedule and obligations, and rush to meet time OR schedule demands and volume requirements.

Accordingly, a methodology which overcomes the shortcomings of prior art is desired.

BRIEF SUMMARY OF THE INVENTION

In one embodiment of the invention, a surgical scalpel handle assembly system and method that requires a surgeon to actively perform a verification process known as a surgical "time out" by requiring surgeon to affirmatively answer "time out" criterion by moving a sequential series of actuators representing criterion embedded In the scalpel handle that upon confirmation of each subsequent criteria such that upon actively confirming three sequential criteria the handle unlocks a blade holder from a scalpel handle and ultimately ejects a blade holder to a position fully exposed from within the handle in an engaged position, ready for blade attachment and surgery. The surgical "time out" verification process on the scalpel handle includes in the pre-operative state exposed visual indicia on the handle that indicate red in three separate visual "windows" corresponding to the three separate "time out" criteria. Upon active confirmation of sliding a knob towards front end of handle for each sequential confirmation of the "time out" criterion by surgeon will show a color change through the visual window within the scalpel handle and will show green. After sliding all three actuators in handle in response to sequentially performing all three "time out" criteria, all the visual indices through windows in handle will display green, and the blade holder will be ejected to a deployed fully exposed, engaged and in a ready for blade attachment cutting position.

In one embodiment of the invention, a surgical scalpel handle assembly system and method that requires a surgeon to actively perform a verification process known as a surgical "time out" by requiring surgeon to affirmatively answer "time out" criterion by moving a sequential series of actuators representing criterion embedded In the scalpel handle that upon confirmation of each subsequent criteria such that upon actively confirming three sequential criteria the handle unlocks a blade holder from a scalpel handle and ultimately ejects a blade holder to a position fully exposed from within the handle in an engaged position, ready for blade attachment and surgery. A battery is disposed in the interior of the scalpel handle having a positive and negative terminal. One end of a positive lead wire is attached to the positive terminal, and one end of a negative lead wire is attached to the negative terminal. The other end of the positive lead wire is attached to a first proximal lead disposed on the first sequential sliding element at the end proximate the battery. A first distal lead is disposed on a first sequential sliding element at the end distal the battery and proximate to an adjacent intermediate sequential sliding element. A conductive material is disposed on the first sequential sliding element connecting the first proximal lead and the first distal lead. Each adjacent sequential sliding elements comprises an intermediate proximal lead disposed at the end proximate the prior sequential sliding element and an intermediate distal lead distal the prior sequential sliding element and proximate to the next adjacent intermediate sequential sliding element. A conductive material is disposed on each intermediate sequential sliding element connecting the intermediate proximal lead and the intermediate distal lead. A final sequential sliding element comprises a final proximal lead disposed at the end proximate the previous intermediate sequential sliding element and an electrical illumination device disposed at the end distal to the adjacent sequential sliding element. One end of the negative lead wire is attached to the illumination device.

The surgical "time out" verification process on the scalpel handle of this embodiment includes in the pre-operative state an exposed visual indicator on final sequential sliding element that has no color indication in a visual "window" through which the illumination device can be observed. Upon active confirmation for each sequential confirmation of the "time out" criterion by surgeon, a plurality of actuators, each extending through one of a plurality of windows on the top exterior surface of the scalpel handle and each attached to and in movable correspondence with one of the sequential sliding elements, is moved towards the front end of handle beginning with the actuator attached to the first sequential sliding element. After sliding all actuators in response to sequentially performing all three "time out" criteria, a circuit is completed by electrical connection of the leads disposed on the sequential sliding elements. The completed circuit causes the illumination device to light and display a green color through a window in the scalpel handle. Simultaneously, the blade holder will be ejected to a deployed fully exposed, engaged and in a ready for blade attachment cutting position.

Using a surgical time out verification process on the scalpel handle can help remove a surgical team's "impulsivity" and hazardous attitude and reduce wrong site wrong patient surgeries. Picking up the scalpel by the surgeon is the last step before cutting the patient's skin and would be the best place to conduct the surgical time out.

OBJECT OF INVENTION

The main object of the present invention is to provide a surgical scalpel handle that prevents performing surgery without first performing a verification process known as a surgical time out.

Another object of the present invention is to provide a surgical scalpel handle that can provide verification process messaging to a surgeon prior to using a surgical scalpel.

Another object of the present invention is to require a surgeon to slide actuator knobs affirmatively on a scalpel handle while performing a surgical time out verification process.

Another object of the present invention is to provide visual indicia to indicate a "stop take a time out status of not performing surgery.

Another object of the present invention is to provide visual indicia to indicate a "go ready for cutting" status of performing surgery.

Yet another object of the present invention is providing a surgical handle that through display messaging is a reminder instrument for surgeon to follow certain protocols.

Yet another object of the present invention is to provide a surgical scalpel that does not release a movable blade holder containing a blade until requisite preceding actions are actuator knobs are moved in sequence.

Yet another object of the present invention is to require a specific set of sequential actuations be performed on the surgical scalpel handle to bring blade into operational "ready for cutting mode."

Yet another object of the present invention is to have the surgical scalpel handle with movable blade holder with no blade attached and contained within front end of surgical scalpel handle to avoid accidental injury when operating surgical scalpel handle until surgery is ready to be performed and blade is then attached.

The present invention is directed to an assembly which contains a surgical scalpel handle and blade assembly system and includes a method that requires a surgeon to actively perform a verification process by requiring surgeon to affirmatively answer "time out" criterion by moving a sequential series of actuator knobs and sliders representing criterion information embedded in the scalpel handle that upon confirmation of each subsequent criteria unlocks a movable blade holder from a scalpel handle to a position fully engaged and ready for blade attachment and in cutting position. The verification process known as a surgical "time out" on the scalpel handle includes in the stand by pre-operative state exposed visual indicia on the handle that indicate red seen in three separate visual "windows" corresponding to the three separate "Stop. Take a Surgical Time Out" criteria.

The procedure for the operation would be such that the surgeon would pick up the scalpel handle safely since the movable blade holder and no blade is attached and the surgeon would read the first criterion. The surgeon would confirm time out criterion with patient or staff and upon confirmation would move the actuator knob from rear to front unlocking subsequent knob distal to it. This would cause the respective visual window in the handle to change from red to green directly underneath that first criterion. The surgeon would repeat this for the next two criteria in order from rear to front. Upon active confirmation of sliding a knob towards front end of handle for each of the "time out" verification by surgeon will show a color change through the visual window within the scalpel handle and will show green affirming all "time out" criterion have been verified and indicating "go." The movable blade holder will be unlocked, ejected, exposed and fixated in position by the prior confirmative actions of the surgeon and enable the surgeon to attach the blade to the blade holder so scalpel will be in a ready for cutting position.

BRIEF DESCRIPTION OF THE DRAWINGS

The various features of the present invention and the manner of attaining them will be described in greater detail with reference to the following description, claims, drawings, wherein reference numerals are reused, where appropriate to indicate a correspondence between the referenced items, and wherein the preferred embodiments of the invention will herein after be described in conjunction with appended drawings to Illustrate and not to limit the invention wherein like designations denote like elements and in which:

FIG. 4*a* shows the upper housing with the bade holder exit hole, FIG. 4*b* shows the inner housing's sliding and locking mechanism with the actuators and blade holder, and FIG. 4*c* shows the lower housing unit showing the guide rails, upper to lower housing engagement feature, lock pin engagement hole and blade holder exit slot;

FIG. 6*a*-6*d* is a schematic representation of a top view of the inside of handle assembly showing the top of sliders and their relationship to each other in three separate positions starting with standby pre-cutting in FIG. 6*a*, and then after each actuator is placed in a confirmatory position in FIGS. 6*b*-6*d* respectively and showing FIG. 6 *d* in ready for cutting position with blade holder ejected;

FIG. 8*a*-8*b* is an isometric view of the inside of blade holder assembly including lock pin and springs and bayonet fitting in two positions standby and ready for cutting position;

FIGS. 10*a*-10*c* are an undersurface bottom view of the exterior of lower housing unit, an undersurface bottom view of the inner housing actuators and blade holder, and an undersurface bottom view of inside of upper housing unit of one embodiment of the invention.

DETAILED DESCRIPTION OF THE PREFERRED EMBODIMENT

The present invention is directed to a surgical scalpel handle assembly system and method for using a scalpel handle assembly to perform a pre-operative verification process known as a surgical "time out". Wrong site and wrong patient surgeries continue to occur in outpatient, inpatient and operative room settings. Despite recommendations and guidelines to require surgeons and their staff to perform a verification process known as a "time out" wherein an active confirmation of the patient's name, procedure and site of procedure are confirmed before proceeding with surgery, wrong site or wrong patient surgeries continue to occur and the predominant cause is failure of surgeon and staff to take a surgical "time out." Impulsivity, workload, carelessness, over scheduling and the need to perform multiple surgeries on multiple patients in the same day contribute to surgeons haste and not taking the time to perform a surgical "time out."

Figure 1:
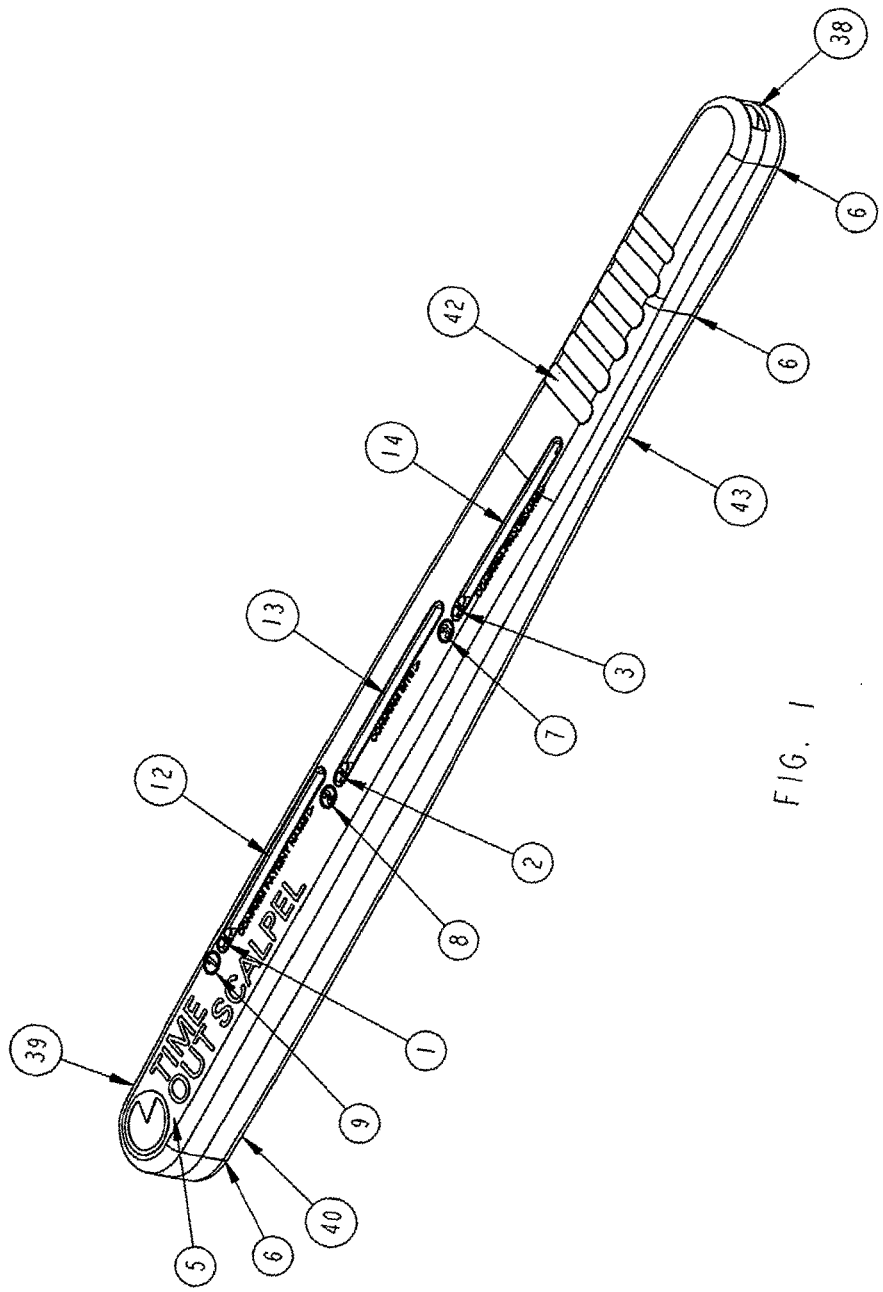
FIG. 1 is an assembled isometric top view of upper housing of a scalpel handle in accordance with a preferred embodiment of the present invention with visual indices shown in the pre-operative stand by position with blade holder exit slot.

The present invention is a surgical scalpel handle assembly system and method for requiring the performance of a "time out" verification process in the scalpel handle prior to surgery before a scalpel handle can be usable for surgery. The unlocking of sequential actuators and sliders on the scalpel handle is required to unlock and eject the blade holder of a surgical handle prior to performing surgery. Using a surgical time out verification process on the scalpel handle can help remove the "impulsivity" and surgeon's hazardous attitude and reduce wrong site wrong patient surgeries. Picking up the scalpel by the surgeon is the last step before cutting the patient's skin and would be the best place to conduct the surgical time out. The surgeon is required to go through a verification process known as a surgical time out. The following is the description of the invention described in detail below with reference to the accompanying drawings:

In FIG. 1, an assembled isometric top view of a scalpel handle in accordance with a preferred embodiment of the present invention with visual indices shown and blade holder contained within handle in the pre-cutting position. The upper housing (39) of the scalpel handle is provided with three groove windows (12, 13, 14) and each groove window in pre operative state shows visual indices red at base of groove window. The blade holder exit slot (38) is provided at the front end of the handle and there is a logo (5) that is provided at the rear of the handle on the upper housing (39). There are three actuator notched knobs (1,2,3) that are positioned on the rear side of each window (12, 13, 14). There are three different time out verification criteria (9,8,7) each inscribed with the numbered "1", "2", and "3" before each window (12,13,14) respectively and with directions and arrow inscribed below each groove window (12, 13, 14) respectively. The arrows below each window (12, 13, 14) direct the user to move the knob rear to front upon active sequential confirmation of a criteria (9, 8, 7) located below each groove window (12, 13, 14) respectively. The upper housing unit (39) contains a finger grip (42) and the lower housing unit (40) contains a contoured grip (43). There are upper and lower unit exterior lines (6) to match both units in proper position. The surgeon must verify each criterion (9, 8, 7) in sequential order to be able to move each subsequent knob (1, 2, 3) from rear to front. Upon affirmatively confirming criterion (9), the surgeon would depress to release knob (1) and then slide knob (1) in a rear to front direction. After knob (1) has been moved to its fullest front position, it will change visual indices through window (12) from red to green and lock into place and release knob (2) so that surgeon will then have to affirmatively confirm criterion (8) to move knob (2) from rear to front. Upon affirmatively confirming criterion (8) and after knob (2) has been moved to its fullest front position, it will change visual indices through window (13) from red to green and it will release knob (3) so that surgeon will have to affirmatively confirm criterion (7) to move knob (3) from rear to front and upon doing so, it will change visual indices through window (14) from red to green.

Figure 2:
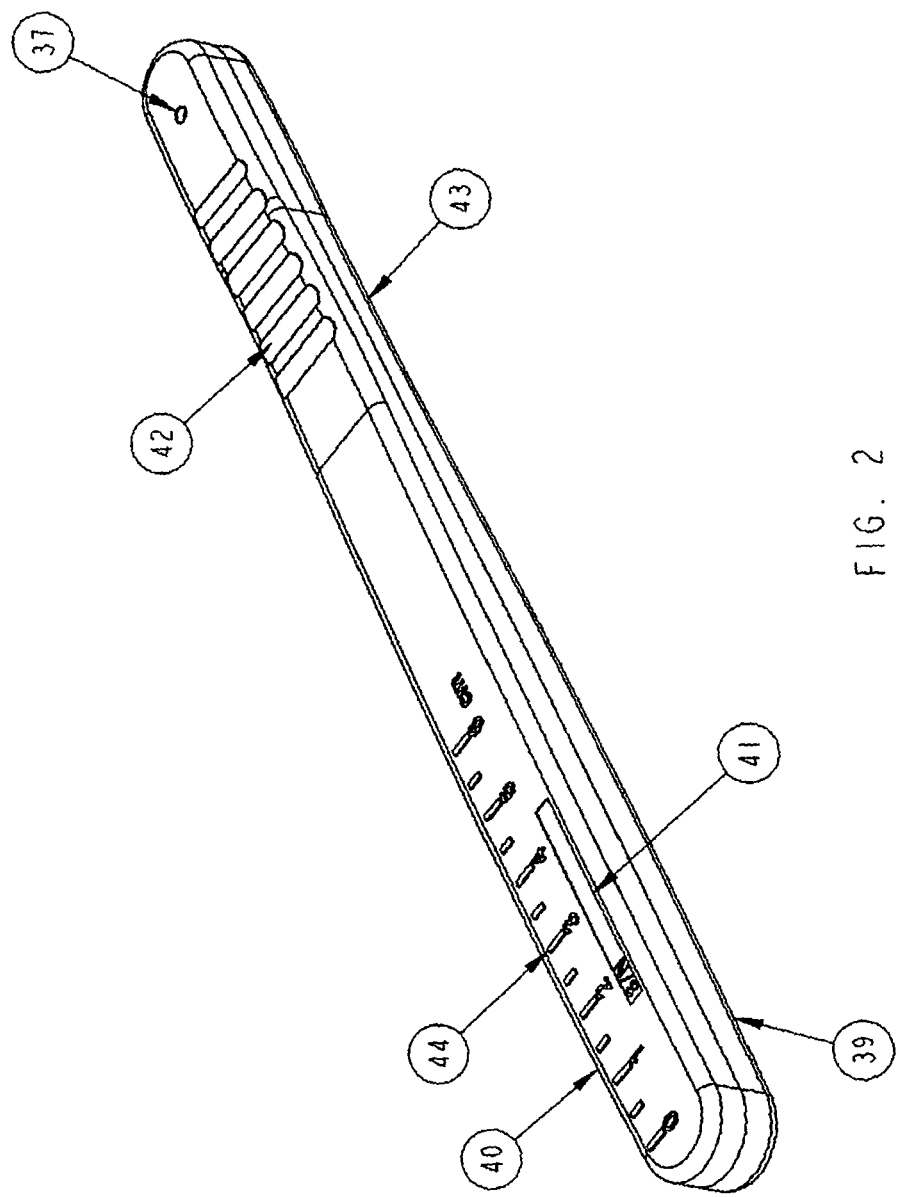
FIG. 2 is an assembled isometric bottom view of lower housing of a scalpel handle in accordance with a preferred embodiment of the present invention in the preoperative stand by position; and FIG. 3*a* through FIG. 3*d* is a top view and schematic representations of the scalpel's handles actuators• in different positions with, windows for the visual indices, showing each view of the handle (3*b*, 3*c*, 3*d*) upon completing each sequential actuator movement In confirmation of criteria one, two and three, respectively with FIG. 3*d* showing all actuators in confirmed position with blade holder fully exposed and engaged in ready for blade attachment and cutting position in accordance with the preferred embodiment.

In FIG. 2, is an assembled isometric bottom view of a scalpel handle and lower housing (40) in accordance with a preferred embodiment of the present invention with blade holder contained within handle in the pre-cutting position. The lower housing (40) contains a contoured grip (43) and finger grips (42) at the front end. There is a small metric ruler (44) on the rear side of lower housing (40) and there is a serial number marking (41) on the rear side of lower housing (40). There is a blade reset hole (37) that is located on the front end of the lower housing (40).

In FIGS. 3a-3d, is a top view and schematic representations of the scalpel handle's actuators in different positions with, windows for the visual indices, showing each view of the handle (3b, 3c, 3d) upon completing actuator movement in confirmation of criteria one, two and three, respectively with FIG. 3d showing all actuators in confirmed position with blade holder fully exposed and engaged in ready for blade attachment and cutting position in accordance with the preferred embodiment. In FIG. 3a a schematic representation of the scalpel's handles actuators (1,2,3) in standby preoperative positions with windows (12, 13, 14) all showing red visual indices. In FIG. 3b, actuator (1) is moved from rear to front upon confirmation of criterion (9) revealing a change in visual indices from red to green in window (12). In FIG. 3c, actuator (2) is moved from rear to front upon confirmation of criterion (8) revealing a change in visual indices from red to green in window (13). In FIG. 3d, actuator (3) is moved from rear to front upon confirmation of criterion (7) revealing a change in visual indices from red to green in window (14) and as a result blade holder (4) is ejected through blade holder slot (38) and scalpel is in ready for blade attachment and cutting position and all windows (12, 13, 14) reveal green indices.

Figures 4A, 4B, 4C:
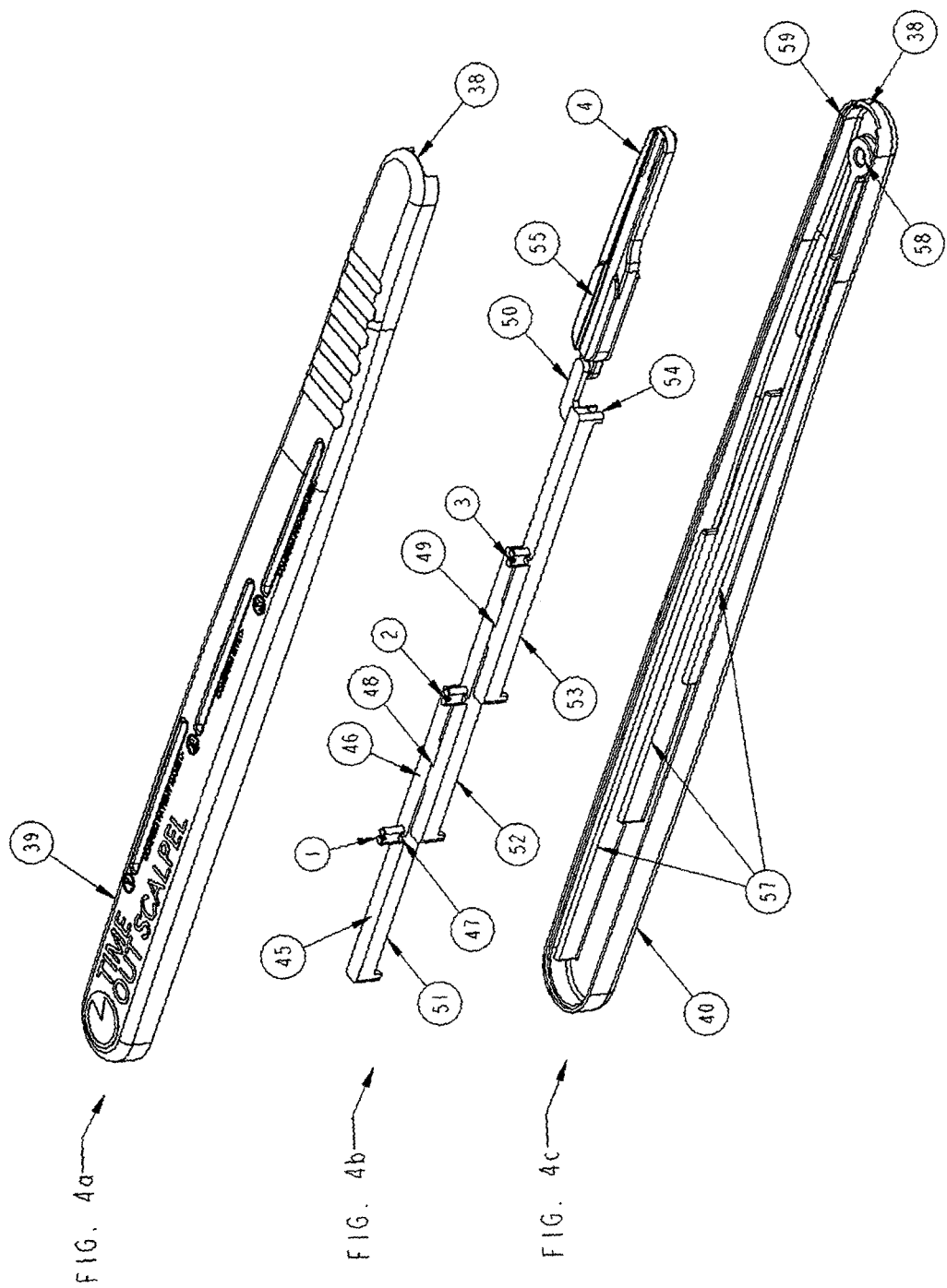
FIG. 4*a*-4*c* is a schematic representation of the scalpel handles housing units, upper, inner and lower housing respectively.

In FIGS. 4a through 4c, a top view schematic representation• of the scalpel handles housing units, upper, inner and lower housing respectively. FIG. 4a shows the upper housing (39) with the blade holder exit hole (38) at front of upper housing of handle. FIG. 4b shows the inner housing in standby pre-operative position with the actuators (1,2,3), sliders (51,52,53) each in relationship to each other in standby pre-cutting position. Each slider (51,52, 53) has an inverse catch element (46,49) to hold all three sliders (51, 52, 53) from sliding. Slider (53) is attached to blade holder (4) via link (50) and blade holder (4) has guide rail grooves (55) to enable blade holder (4) to move forward steadily and be ejected through blade holder exit hole (38) upon sequential confirmation of all criteria (9,8,7) and sequential movement of all actuators (1,2,3) and corresponding sliders (51, 52, 53). In FIG. 4c the lower housing unit (40) showing the guide rails (57) that enable the sliders (51,52,53) to move from rear to front steadily upon each subsequent confirmation of criteria (9,8,7) by sequential movement of actuators (1,2,3) and corresponding sliders (51,52,53) from rear to front along guide rails (57) respectively. There is a lock pin engagement hole (58) located at the front of the inner lower housing unit (40) for the loaded lock spring (65) and lock pin (64) see on FIG. 7 to lock the blade holder (4) firmly in place upon ejection from exit hole (38). The lower housing unit (40) contains upper to lower housing engagement feature (59) to enable handle body upper and lower housing units to be assembled.

Figures 5A, 5B, 5C:
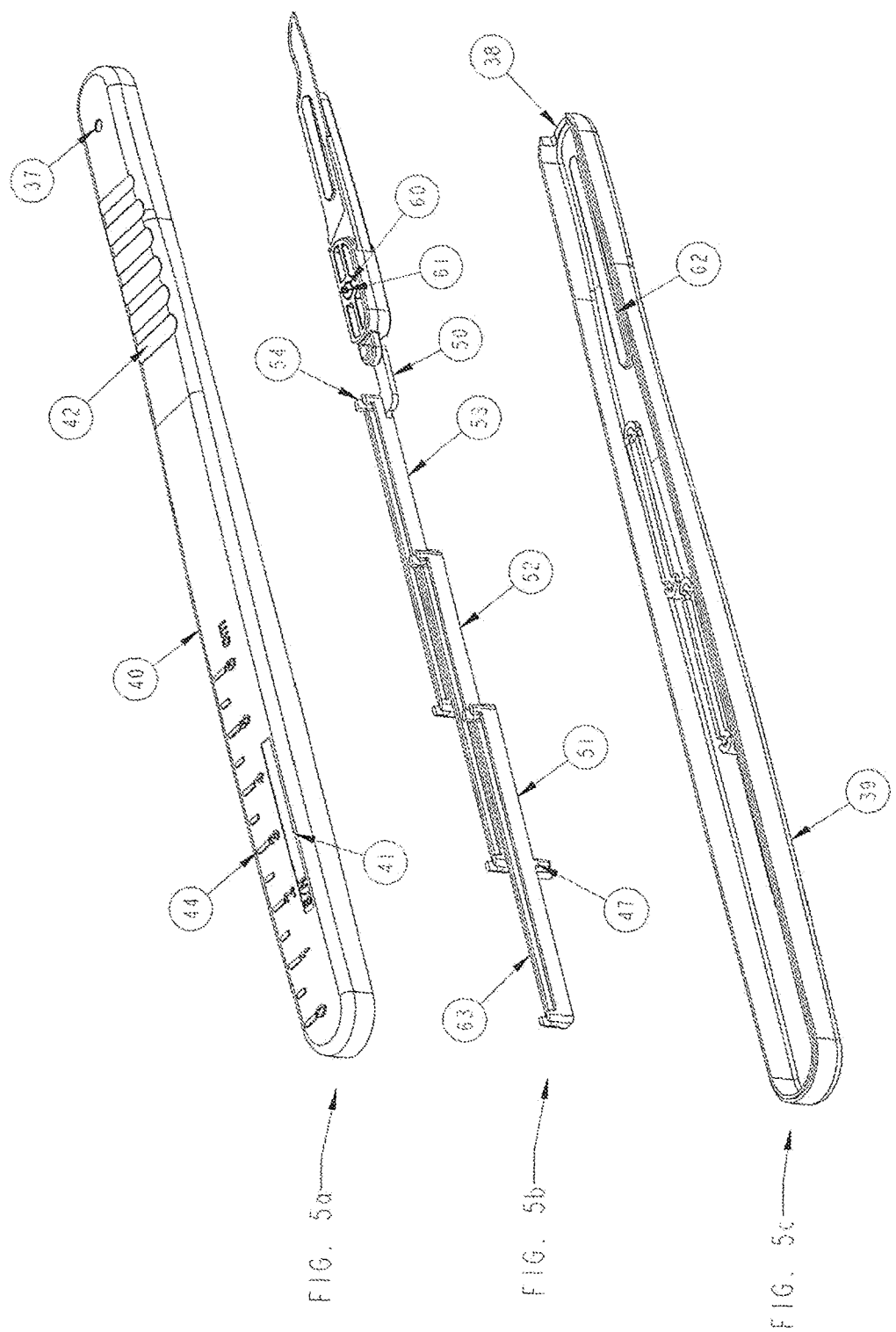
FIG. 5*a*-5*c* is an undersurface bottom view of the exterior of lower housing unit, an undersurface bottom view of the inner housing actuators and blade holder, and an undersurface bottom view of inside of upper housing unit.

In FIG. 5a-5c, is an undersurface bottom view of the exterior of lower housing unit (40), a undersurface bottom view of the inner housing sliders (51, 52, 53) and blade holder (4), and an undersurface bottom view of inside of upper housing unit (39). In FIG. 5a, the lock pin reset access hole (37) is provided so after surgery, a blade may be removed from blade holder, and by inserting small instrument into reset access hole (37) a reset of all sliders (51, 52, 53) and blade holder (4) to original stand by pre-operative position may be obtained in order that blade handle may be reposable and reusable after sterilization. In FIG. 5b, the undersurface of sliders (51, 52, 53) have matching slider guides (54) on front and rear ends so sliders may slide along slider rails (57). Ribs (63) are provided on sliders designed to control deflection force to overcome detent positions on sliders (51, 52, 53). Also, there is provided a blade holder (4) with a lock pin (60) with a loaded lock pin spring (61) so that upon forward ejection of blade holder (4) through exit hole (38), lock pin (60) locks into lock pin engagement hole (58) on lower housing (40) to prevent further movement of blade holder (4). There is also a detent feature (47) on sliders to prevent forward progression of sliders as detent mates with matching detent feature (63) on upper housing noted in FIG. 5c. In FIG. 5c, the inside of the upper housing unit (39) is shown. The blade holder assembly guide rail (62) Is provided for guiding forward the blade holder (4) upon ejection through exit hole (38).

In FIGS. 6a through 6d, a schematic representation of a top view of the inside of handle assembly in four different conditions. In FIG. 6a, the first condition is shown in stand by pre-cutting position with the top of sliders (51, 52, 53) provided with a catch (48) for sliders (51) and (52) and another catch (49) provided for sliders (52) and (53) to prevent forward motion of respective sliders. In FIG. 6b, slider (51) is moved from rear to front upon confirming criterion (9) and stopped at end of slider guide rail (57) and releasing catch (48) and releasing slider (52) from a fixed non-movable 16 position. In FIG. 6c upon confirmation of criterion (8), slider (52) is moved forward and resets catch (48) between slider (51) and (52) but releases catch (49) from slider (52) and (53) rendering slider (53) movable. In FIG. 6d, slider (53) is moved forward after confirming criterion (7) and resets catch (49) with slider (52) and simultaneously moves link (50) and blade holder (4) forward along guide rails (62) until loaded lock pin spring (61) and lock pin (60) engages with lock pin engagement hole (58) and stabilizes blade holder from further movement forward or lateral. The condition of the handle in FIG. 6d is ready for blade attachment and cutting position.

Figure 7:
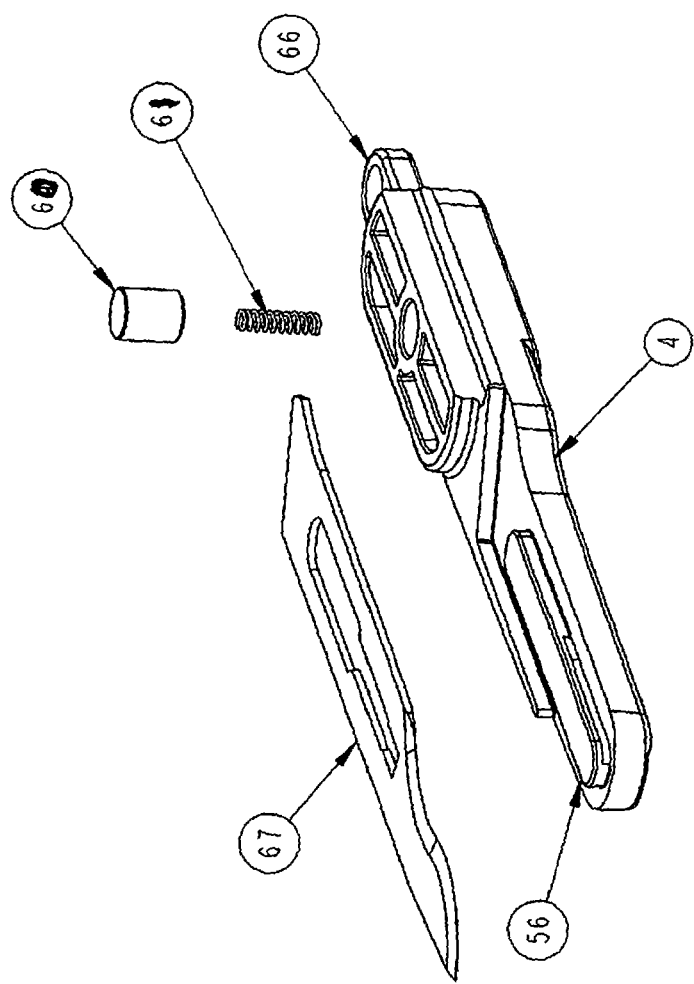
FIG. 7 is a detailed isometric view of the blade holder assembly including lock pin and springs and bayonet fitting.

In FIG. 7 a detailed isometric view of the blade holder assembly including lock pin (60) and lock spring (61), bayonet fitting (56) and blade holder (4) is-provided. The slider connection feature (66) is provided to attach to link (50). A blade (67) is shown for illustrative purposes to show that it attaches to bayonet fitting (56) when handle would be in ready for blade attachment and cutting position.

In FIGS. 8a-8b an isometric view of the inside of front portion of handle and blade holder (4) assembly and relationship to lock pin (60) in two conditions. In FIG. 8a, the condition of the handle would be in stand by pre-cutting condition with lock pin (60) and lock spring (61) loaded but not engaged. In FIG. 8b, upon forward ejection of blade holder (4), loaded lock spring (61) and lock pin (60) engage in lock pin engagement hole (58) enabling stabilization of blade holder (4) when ejected out of exit slot (38).

Figure 9:
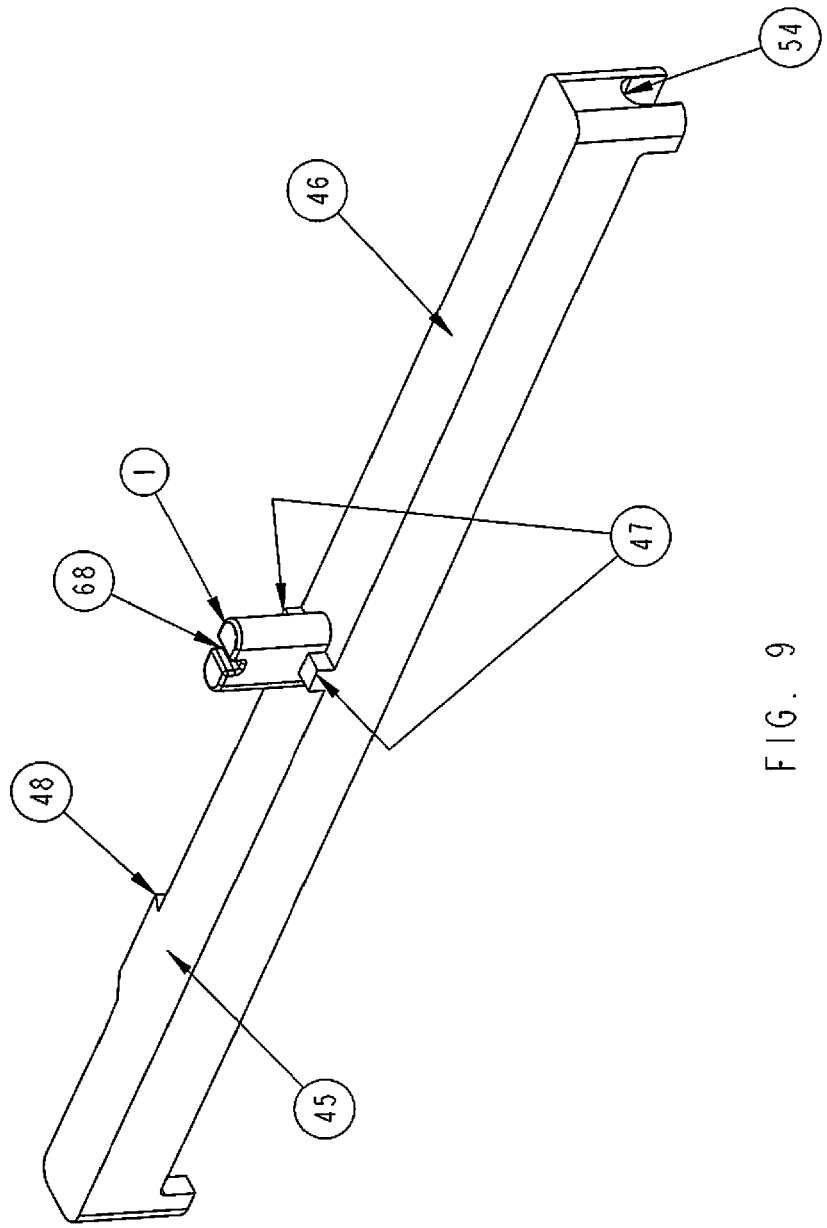
FIG. 9 is an isometric view of an actuator and accompanying slider.

In FIG. 9, an isometric view of an actuator (1) and slider (51) and visual indices is provided for illustration purposes as sliders (52) and (53) have similar features and all visual indices are provided showing the green side (48) on the top and to the rear of actuator knob (1) on slider (51) and showing the red side (46) on top and in front of actuator knob (1) on slider (51). There is a finger nail catch slot (68) provided for on actuator knob (1). The guide rail engagement feature (54) is provided to demonstrate how sliders slide along guide rails (57). The catch (48) is shown on slider (51) to stop slider from moving forward upon catching on adjacent slider (52). There is also a detent 17 feature (47) on sliders to prevent forward progression of sliders as detent mates with matching detent feature (63) on upper housing noted in FIG. 9c.

In FIG. 10a-10c, an undersurface bottom view of the exterior of lower housing unit (1040), an undersurface bottom view of the inner housing sliders (1051, 1052, 1053) and blade holder (104), and an undersurface bottom view of inside of upper housing unit (1039) is shown. In FIG. 10a, lower housing (1040) contains finger grips (1042) at the front end. There is a small metric ruler (1044) on the rear side of lower housing (1040) and there is a serial number marking (1041) on the rear side of lower housing (1040). A lock pin reset access hole (1037) is provided so after surgery, a blade may be removed from blade holder, and by inserting small instrument into reset access hole (1037) a reset of all sliders (1051, 1052, 1053) and blade holder (104) to original stand by pre-operative position may be obtained in order that blade handle may be reposable and reusable after sterilization. In FIG. 10b, the undersurface of sliders (1051, 1052, 1053) have matching slider guides (1054) on front and rear ends so sliders may slide along slider rails. Ribs (1063) are provided on sliders designed to control deflection force to overcome detent positions on sliders (1051, 1052, 1053). Also, there is provided a blade holder (104) with a lock pin (1060) with a loaded lock pin spring (1061) so that upon forward ejection of blade holder (104) through exit hole (1038), lock pin (1060) locks into lock pin engagement hole (1058) on lower housing (1040) to prevent further movement of blade holder (104). There is also a detent feature (1047) on sliders to prevent forward progression of sliders as detent mates with matching detent feature (1063) on upper housing noted in FIG. 10c. In FIG. 10c, the inside of the upper housing unit (1039) is shown. The blade holder assembly guide rail (1062) is provided for guiding forward the blade holder (104) upon ejection through exit hole (1038).

A battery (1070) is disposed in the interior of upper housing unit (1039) and is attached to a positive lead wire (1072) and a negative lead wire (1073). Each slider (1051, 1052, 1053), also called sequential sliding element, comprises a first lead (1075) and a second lead (1076). First lead (1075) and second lead (1076) of each slider (1051, 1052, 1053) are electrically connected by electrical conducting material (1077). Positive lead wire (1072) is connected to first lead (1075) of the first slider (1051). The final slider (1053), or sequential sliding element, comprises an illumination device (1080) in electrical connection with electrical conducting material (1077). Negative lead wire (1073) is electrically connected to second lead (1076) on the final slider (1053), or sequential sliding element.

While this invention has been particularly shown and described in reference to the preferred embodiments thereof, it would be understood by those skilled in the art that various changes in form and detail may be made therein without departing from the scope and spirit of the invention encompassed by the impended claims. Although the embodiments have been ~ascribed in reference to a scalpel handle and blade and system and method for taking a surgical time out or any surgical verification process, the assembly, system and method according to the embodiments of the present invention may also apply to any surgical instrument or device, disposable or non-disposable, that would be used on or in the body for treating, removing or diagnosing including but not limited to surgical laser instruments, endoscopes, curettes, surgical wire instruments, scalpels, and other excisional surgical instruments. The scope of the invention also extends to various combinations and modifications that may fall within the spirit of the appended claim.

The invention claimed is:
1. A surgical scalpel handle and a blade holder assembly for requiring the performance of a verification process to ready the surgical scalpel handle for surgery comprising:
    a scalpel handle; and
    a blade holder;
wherein the scalpel handle comprises:
    a top exterior surface;
    a bottom exterior surface substantially parallel to the top exterior surface;
    two sidewalls, a first end and a second end disposed substantially perpendicular to and between the top exterior surface and the bottom exterior surface;
    a hollow interior cavity defined as the space between the top exterior surface, the bottom exterior surface, the two sidewalls, the first end and the second end;
    a blade holder slot in the first end;
    a battery disposed in the hollow interior cavity comprising a positive terminal and a negative terminal;
    a positive lead wire connected to the positive terminal;
    a negative lead wire connected to the negative terminal;

a plurality of windows disposed on the top exterior surface of the scalpel handle, each window of the plurality of windows corresponding to a step in the verification process;

a plurality of sequential sliding elements comprising a first sequential sliding element that is the most distal of the sequential sliding elements from the first end of the scalpel handle, a final sequential sliding element that is the most proximate of the sequential sliding elements to the first end of the scalpel handle and one or more intermediate sequential sliding elements situated between the first sequential sliding element and the final sequential sliding element, wherein the plurality of sequential sliding elements are disposed in the hollow interior cavity of the scalpel handle, wherein each of the sequential sliding elements comprises a first side wall and a second side wall, wherein the first side wall of the first sequential sliding element and each of the intermediate sequential sliding elements comprises a first guide rail groove, wherein the second side wall of each of the intermediate sequential sliding elements and the final sequential sliding element comprises a second guide rail groove, wherein the first side wall of the first sequential sliding element and each of the intermediate sequential sliding elements further comprises a first detent element disposed on each of the first and intermediate sequential sliding elements, wherein the second side wall of each of the intermediate sequential sliding elements and the final sequential sliding element comprises a second detent element disposed on each of the sequential and final sliding elements, wherein the first detent element of each of the first and intermediate sequential sliding elements is in sliding cooperation with the second guide rail groove of the adjacent intermediate or final sequential sliding element that is more proximal to the first end of the scalpel handle, wherein the second detent element of each of the sequential sliding elements is in sliding cooperation with the first guide rail groove of each of the sequential sliding elements that is more distal from the first end of the scalpel handle, whereupon each sequential sliding element moves within the respective first guide rail groove and second guide rail groove between an initial position distal from the first end of the scalpel handle and a final position proximal the first end of the scalpel handle;

an illumination device disposed on the distal end of the final sequential sliding element, wherein the illumination device is attached to the negative lead wire, wherein the illumination device is viewable through the window corresponding to the final position of said final sequential sliding element in the hollow interior;

a first lead and a second lead disposed on each end of the plurality of sequential sliding elements, wherein the first lead and second lead of each of the plurality of sequential sliding elements is connected by an electrically conductive material, wherein the first lead of the first sequential sliding element is attached to the positive lead wire; and a plurality of actuators extending through one of the plurality of windows in the top exterior surface of the scalpel handle, each of the actuators attached to and in movable correspondence with one of the plurality of sequential sliding elements, whereupon movement of each of the actuators from the second end of the scalpel handle toward the first end of the scalpel handle moves the corresponding one of the sequential sliding elements in the direction of the first end of the scalpel handle from its initial position distal from the first end of the scalpel handle to its final position proximate the first end of the scalpel handle, whereupon movement of each of the sequential sliding elements ceases when the first detent element of the sequential sliding element being moved engages with the second detent element of the adjacent sequential sliding element, whereupon the second lead of each sequential sliding element electrically mates with the first lead of the adjacent sequential sliding element, whereupon a circuit is formed by movement of all of the sequential sliding elements to each of their final positions and lighting the illumination device, wherein the blade holder is disposed in the hollow interior cavity of the scalpel handle on the end of the final sequential sliding element proximal the first end of the scalpel handle, wherein movement of the actuator corresponding to the final sequential sliding element causes the final sequential sliding element to move toward the first end of the scalpel handle, whereupon the blade holder is moved through the blade holder slot, whereupon movement of the blade holder through the blade holder slot causes a lock pin disposed on the blade holder to engage in a lock pin engagement hole disposed in a wall of the hollow interior cavity, whereupon the movement of the blade holder is blocked from returning into the hollow interior cavity.

2. The surgical scalpel handle and blade holder assembly of claim 1, wherein the illumination device comprises a green LED bulb.

3. The surgical scalpel handle and blade holder assembly of claim 2, wherein the number of the plurality of sequential sliding elements corresponds to a predetermined number of verification pre-operative criteria.

4. The surgical scalpel handle and blade holder assembly of claim 2, further comprising interactive instructional inscriptions on the top exterior surface of the scalpel handle that correspond to each of the verification pre-operative criteria.

5. The surgical scalpel handle and blade holder assembly of claim 2, wherein the number of verification pre-operative criteria comprise three criteria.

6. The surgical scalpel handle and blade holder assembly of claim 1, further comprising a reset access hole in the bottom exterior surface of the scalpel handle allowing access to the lock pin that is engaged in the lock pin engagement hole, whereupon depression of the lock pin causes movement of the blade holder back into the hollow interior cavity whereupon the blade holder and plurality of sequential sliding elements are reset to their initial positions most distal from the first end of the scalpel handle prior to movement of movement of the plurality of sequential sliding elements.

7. The surgical scalpel handle and blade holder assembly of claim 1, further comprising commercial messaging and signage displayed on the exterior of the scalpel handle.

\* \* \* \* \*